United States Patent [19]

Purcell et al.

[11] Patent Number: 4,701,466
[45] Date of Patent: Oct. 20, 1987

[54] DIBENZ[BE]OXEPIN-ACETIC ACID DERIVATIVES, THE PREPARATION THEREOF AND THEIR APPLICATION IN THERAPY

[75] Inventors: Thomas Purcell, Montfort l'Amaury; Lydia Zard, Gif s/Yvette, both of France

[73] Assignee: Synthelabo, Paris, France

[21] Appl. No.: 851,114

[22] Filed: Apr. 10, 1986

[30] Foreign Application Priority Data

Apr. 11, 1985 [FR] France ............................. 8505425

[51] Int. Cl.$^4$ .................. C07D 313/12; A61K 31/335
[52] U.S. Cl. .................................... 514/450; 549/354; 549/355; 560/61
[58] Field of Search .................... 549/354; 514/450

[56] References Cited

U.S. PATENT DOCUMENTS 4,356,186 10/1982 Uno et al. ........................... 514/450
4,585,788 4/1986 Helsley et al. ...................... 514/450

Primary Examiner—Norma S. Milestone
Attorney, Agent, or Firm—Wegner & Bretschneider

[57] ABSTRACT

Compounds of general formula

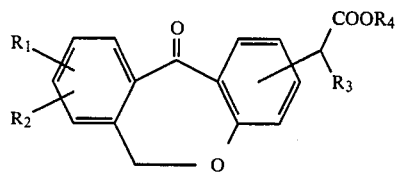

in which
$R_1$, taken separately, denotes a hydrogen atom or a $C_1$–$C_4$ alkyl group, and
$R_2$, taken separately, denotes a hydrogen atom, a $C_1$–$C_4$ alkyl group or a phenylthio or phenylsulphonyl group, or alternatively
$R_1$ and $R_2$ together form an ethano bridge or, together with the two carbon atoms 8 and 9, form a fused benzene ring,
$R_3$ denotes a hydrogen atom or a methyl group and
$R_4$ denotes a hydrogen atom, a $C_1$–$C_4$ alkyl group or a cation of a base which is acceptable in pharmacology, the group $CH(R_3)COOR_4$ being at position 2 or 3. have uses in treatment of inflammation, pain and undesirable platelet aggregation.

11 Claims, No Drawings

DIBENZ[BE]OXEPIN-ACETIC ACID DERIVATIVES, THE PREPARATION THEREOF AND THEIR APPLICATION IN THERAPY

The present invention relates to dibenz[be]oxepina-cetic acid derivatives, the preparation thereof and their application in therapy.

The compounds of the invention correspond to the general formula I,

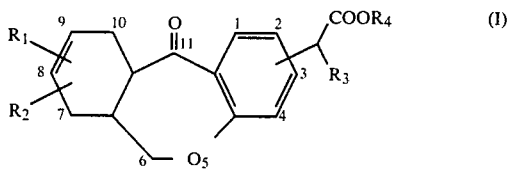

in which $R_1$, taken separately, denotes a hydrogen atom or a $C_1$–$C_4$ alkyl group, and $R_2$, taken separately, denotes a hydrogen atom, a $C_1$–$C_4$ alkyl group or a phenylthio or phenylsulphonyl group, or alternatively $R_1$ and $R_2$ together form an ethano bridge or, together with the two carbon atoms 8 and 9, form a fused benzene ring, $R_3$ denotes a hydrogen atom or a methyl group and $R_4$ denotes a hydrogen atom, a $C_1$–$C_4$ alkyl group or a cation of a base which is acceptable in pharmacology, the group $CH(R_3)COOR_4$ being at position 2 or 3.

The various isomeric forms which can be taken by the compounds of formula I also form part of the invention. The compounds can, in effect, possess cis or trans isomerism with respect to the axis defined by the carbon atoms 6a and 10a. Furthermore, when $R_3$ denotes a methyl group, the carbon atom bearing it is chiral, as are the atoms 7 and 10 when they bear a methyl group.

Among the compounds of the invention, the preferred compounds are those in the formula of which $R_3$ and $R_4$ each denote a hydrogen atom, and more especially those in the formula of which $R_1$ and $R_2$ each denote, simultaneously, a hydrogen atom or a methyl group, preferably bound at positions 8 and 9.

According to the invention, the compounds of formula I can be prepared according to the scheme given on the following page.

A halogenated ester of formula II, in which R' denotes a $C_1$–$C_4$ alkyl group, is first reacted with a hydroxyphenylacetate of formula III, in which R" denotes a $C_1$–$C_4$ alkyl group and $R_3$ is as defined above, and the diester obtained, of formula IV, is then hydrolysed to the diacid of formula V. The latter is then cyclized in the conventional manner, for example in the presence of the thionyl chloride, to obtain the benz[b]oxepin-2-acetic derivative of formula VI. The latter is protected by esterifying it (formula VII) with an alkanol of formula ROH, R being a $C_1$–$C_4$ alkyl group and then, passing through the O-trimethylsilyl intermediate, dehydrogenation is peformed, giving the ester of formula VIII.

The latter is finally subjected to a Diels-Alder reaction with a butadiene of formula IX, in which $R_1$ and Scheme

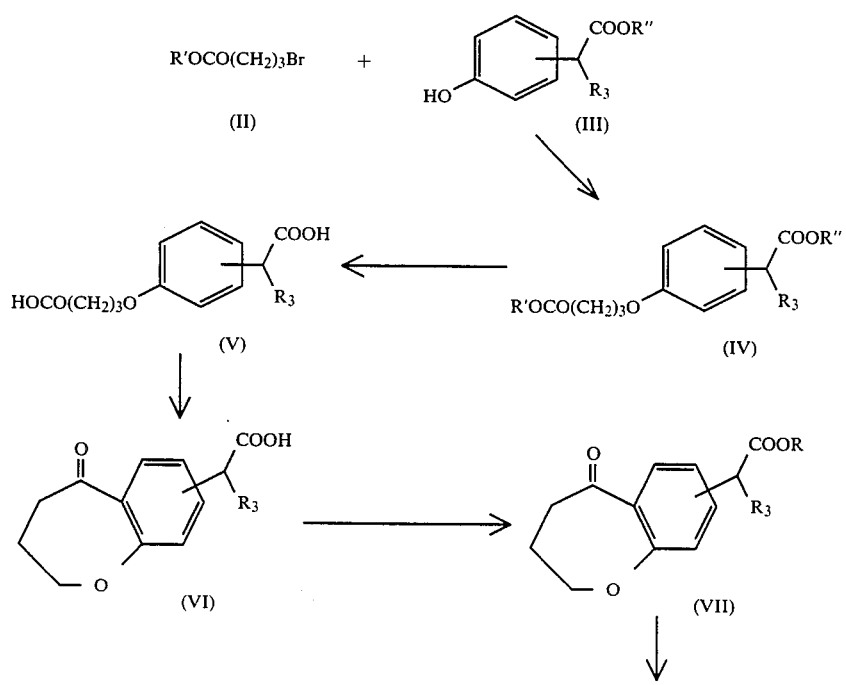

Scheme -continued

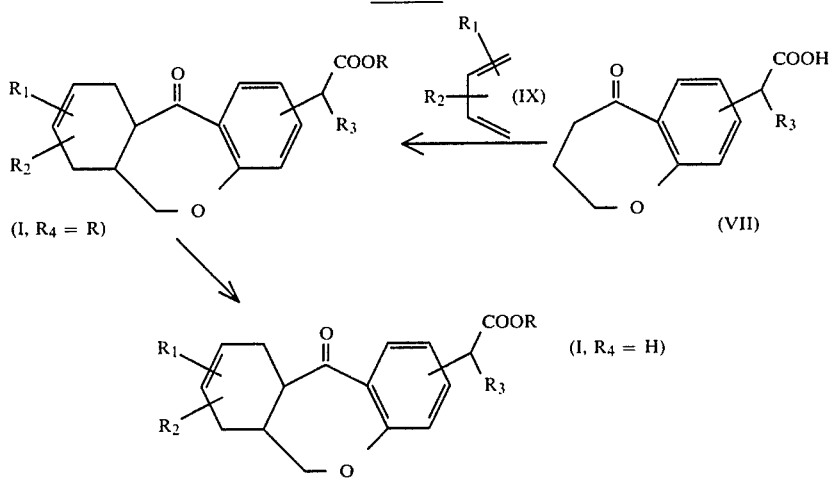

$R_2$ as defined above, thereby producing an ester of formula I ($R_4$ being a $C_1$-$C_4$ alkyl group) which can be hydrolysed to obtain an acid of formula I ($R_4$ being a hydrogen atom).

When it is desired to prepare compounds of formula I in which $R_3$ denotes a methyl group, it is also possible to start with an acetic derivative of formula III in which $R_3$ denotes hydrogen, and insert in the process and α-methylation state, preferably a methylation of the ester of formula VII, before the Diels-Alder reaction.

Finally, if it is desired to separate the enantiomers, it is possible, for example, to react an acid of formula I ($R_4$=H) with one enantiomer of an optically active base, separate the enantiomeric salts thereby obtained by fractional crystallization and liberate the acids from the two separate fractions.

The results of pharmacological tests presented below show that the compounds of the invention can be used as active substances in drugs and pharmaceutical compositions which are usable for the treatment of inflammations of various origins, for the treatment of pain and for the treatment of platelet aggregation.

For this purpose, they can take any form suitable for enteral of parenteral administration, for example the form of tablets, gelatin capsules, dragées, syrups, suppositories, suspensions to be taken by mouth or injectable suspensions, in combination with suitable excipients.

The daily dosage can range from 50 to 1000 mg of active substance.

Accordingly, the invention also provides a method for treating inflammation, pain and undesirable platelet aggregation comprising administering a sufficient, non-toxic amount of a compound of formula (I) to a human or other mammal in need of such treatment.

The invention further provides a pharmaceutical composition comprising a compound of formula (I) and a diluent or carrier therefore; the composition may optionally be presented in unit dosage form.

The examples which follow illustrate in a detailed manner the preparation of a few compounds according to the invention. The microanalyses and the IR and NMR spectra confirm the structures of the compounds obtained.

EXAMPLE 1

11-Oxo-6,6a,7,10,10a,11-hexahydrodibenz[be]oxepin-2-acetic acid (a) Ethyl (4-hydroxyphenyl)acetate.

A mixture of 400 g of (4-hydroxyphenyl)acetic acid, 2.5 l of ethanol and 30 ml of 96% strength sulphuric acid is heated under reflux for 5 h. The mixture is evaporated to dryness, and the residue is taken up with 1 l of dichloromethane and the solution is washed with saturated sodium bicarbonate solution and then with water. The organic phase is dried and evaporated. An oil remains.

(b) Ethyl 4-(4-ethoxycarbonylmethylphenoxy)-butanoate.

45 g of sodium are reacted with 1.6 l of ethanol. 279 g of the ester prepared above are added, followed by 270 ml of ethyl 4-bromobutanoate, and the mixture is heated under reflux for 10 h. The sodium bromide is separated by filtration, the filtrate is evaporated and the residue washed with water and taken up with dichloromethane. The organic phase is washed with sodium hydroxide and then with water, and dried, filtered and evaporated. An oil remains.

(c) 4-(4-Carboxymethylphenoxyl)butanoic acid.

A mixture of 640 g of the oil obtained in (b) above is heated under reflux with 624 ml of 30% strength sodium hydroxide in 1.3 l of water for 6 h. The mixture obtained is acidified, and the beige precipitate is separated by filtration, washed with petroleum ether and dried.

(d) 5-Oxo-2,3,4,5-tetrahydrobenz[b]oxepin-7-acetic acid.

A mixture of 50 g of the diacid prepared above and 500 g of polyphosphoric acid is heated to 90° C. for ¾ h. The mixture is poured into ice-cold water, alkalinized with 33% strength sodium hydroxide to pH 10, and heated, and the aqueous phase is acidified to pH 3 and extracted with dichloromethane. The organic phases are combined, dried and filtered, and the solvent is evaporated off. An oil remains.

(e) Methyl 5-oxo-2,3,4,5-tetrahydrobenz[b]oxepin-7-acetate.

A mixture of 33 g of the above acid, 200 ml of methanol and 3 ml of sulphuric acid are heated under reflux for 4 h. The solvent is evaporated and the residual oil distilled. A transparent oil is collected.

(f) Methyl 5-oxo-2,5-dihydrobenz[b]oxepin-7-acetate.

To a mixture of 60 g of the ester, from (e) above, 500 ml of dichloromethane and 145 ml of triethylamine, 40 ml of iodotrimethylsilane are added while the temperature is maintained at below 20° C., under an atmosphere of argon, and the mixture is allowed to stand at room temperature. The solvent is driven off, the residue is taken up in ether, the insoluble salts are filtered off and the ether is evaporated off. To a suspension of 77 g of dichlorodicyanoquinone in 1 l of benzene, 15 ml of hexamethyldisilazane are added followed, in a single portion, by the above evaporation residue, and the mixture is stirred for 2 h. The solvent is evaporated off and the residue chromatographed on silica, eluting with a 20:8 ethyl acetate/cyclohexane mixture. A reddish-brown oil is collected.

(g) Methyl 11-oxo-6,6a,7,10,10a,11-hexahydrodibenz[be]oxepin-2-acetate.

A mixture of 2.5 g of the oil from (f) above and 1.8 g of butadiene are heated to 170° C. in 15 ml of toluene for 40 h. The solvent is driven off and the residue chromatographed on silica, eluting with a 90:10 cyclohexane/ethyl acetate mixture.

(h) 11-Oxo-6,6a,7,10,10a,11-hexahydrodibenz[be]oxepin-2-acetic acid.

The ester from (g) above is hydrolyzed by heating 1.5 g of its with 0.63 g of 30% strength sodium hydroxide at 50° C. in 17 ml of water and 17 ml of methanol, in the conventional manner. An oil is finally obtained which is left to crystallize in petroleum ether giving the title product melting point: 112°–133° C.

EXAMPLE 2

8,9-Dimethyl-11-oxo-6,6a,7,10,10a,11-hexahydrodibenz[be]oxepin-3-acetic acid (a) 5-Oxo-2,3,4,5-tetrahydrobenz[b]oxepin-8-acetic acid.

Starting with (3-hydroxyphenyl)acetic acid and working as in the stages 1a and 1c above, the 4-(3-carboxymethylphenoxy)butanoic acid is obtained in the form of an oil. 50 g of this are introduced into 500 ml of benzene with 60 ml of thionyl chloride and a trace of dimethylformamide, and the mixture is heated for 2 h under reflux. The solvent is driven off and an oil collected. The latter is dissolved in 400 ml of dichloromethane and added dropwise to a suspension of 37 g of aluminium chloride in 1 l of dichloroethane, the temperature being maintained at between −5° and +5° C. The mixture is stirred for 15 minutes at 0° C., and then hydrolyzed on ice, acidified and extracted with dichloromethane, After conventional treatment, and oil is collected.

(b) 8,9-Dimethyl-11-oxo-6,6a,7,10,10a,11-hexahydrodibenz[be]oxepin-3-acetic acid.

By working as in Examples 1e to 1h, but using the oil in (a) above and Diels-Alder reaction, however, with 2,3-dimethylbutadiene, a compound is obtained whcih melts at 168°–170° C.

(c) Enantiomers of 8,9-dimethyl-11-oxo-6,6a,7,10,-10a,11-hexahydrodibenz[be]oxepin-3-acetic acid.

57.65 g (0.19 mole) of the racemate obtained in b) above and 61.6 g (0.19 mole) of quinidine are dissolved in 800 ml of acetonitrile, and the solution is heated under reflux. The heating is stopped and 30 ml of water are added. A few crystals appear rapidly, and the precipitate then solidifies. After complete cooling, the mother liquor is separated by filtration and retained, and the isolated crystals are dried. They are recrystallized in a mixture of 450 ml of acetonitrile and 50 ml of water, heating the solution to reflux and then allowing it to cool very slowly. After filtration and drying of the precipitate, the acid is liberated by treating the crystals with 10% strength hydrochloric acid, adding a minimum amount of dichloromethane to obtain a solution. The organic phase is separated and washed with saturated sodium chloride solution, and the solvents are driven off under vacuum. The residue is taken up with 200 ml of a 1:1 mixture of ethyl acetate and acetone, the solution is heated to reflux and allowed to cool slightly, and the crystals are separated by filtration and dried. Brilliant white crystals are collected of the dextrorotatory enantiomer of the title product, melting point: 168°–170° C. $[\alpha]_D^{20} = +17.6°$ C. (c=1.0035, CHCl$_3$)

The mother liquor originating from the salification with quinidine is concentrated and treated with 10% strength hydrochloric acid, and the mixture is extracted with ethyl ether. The ether phase is separated and evaporated, and the residue is crystallized in 200 ml of a 1:1 mixture of ethyl acetate and acetone. The purification is completed as for the dextrorotatory enantiomer affording the laevorotatory enantiomer of the title product, melting point: 168°–170° C. $[\alpha]_D^{20} = -18.3°$ (c=1.002, CHCl$_3$)

EXAMPLE 3

α-Methyl-11-oxo-6,6a,7,10,10a,11-hexahydrodibenz[be]oxepin-3-acetic acid (a) Methyl 5-oxo-2,3,4,5-tetrahydrobenz[b]oxepin-8-acetate.

42 g of the acid obtained according to Example 2a is esterified by heating it for 2 h under reflux in 500 ml of methanol in the presence of 5 ml of concentrated sulphuric acid. The mixture is evaporated to dryness and the residue is taken up with a mixture of dichloromethane and saturated aqueous sodium carbonate solution, the organic pahse is separated, washed and dried, the inorganic solid is separated by filtration and the filtrate is evaporated. An oil remains which is distilled under vacuum.

(b) Methyl α-Methyl-5-oxo-2,3,4,5-tetrahydrobenz[b]oxepin-8-acetate.

Lithium diisopropylamide is prepared by mixing, in 100 ml of tetrahydrofuran, 3.11 ml of diisopropylamine and 17.6 ml of n-butyllithium at −30° C.

The mixture is cooled to −70° C. and a solution of 2.34 g of the ester prepared in (a) above, in 20 ml of tetrahydrofuran, is slowly added thereto; an orange-yellow precipitate is formed, and the suspension is stirred for 2 h. 0.74 ml of iodomethane is then added, the mixture is stirred for 30 minutes at −50° C. and a solution is obtained.

The mixture is allowed to return to room temperature and is stirred for a further 30 minutes, and the solution is then cooled to 0° C. and 5 ml of saturated ammonium chloride solution and 20 ml of 5% strength hydrochloric acid are added thereto.

200 ml of water are added and the mixture is extracted twice with 200 ml of dichloromethane. The organic phases are separated, combined, dried and evaporated. An oil remains which is purified by chromatography on a silica column, eluting with a 3:7 ethyl acetate/cyclohexane mixture. A colourless oil is obtained.

(c) α-Methyl-11-oxo-6,6a,7,10,10a,11-hexahydrodibenz[be]oxepin-3-acetic acid.

The procedure is carried out under conditions similar to those described in Example 1f to 1h, using the oil obtained in (b) above, affording the title product, melting point: 158°–160° C.

The table which follows illustrates the structures and physical properties of some compounds according to the invention.

TABLE

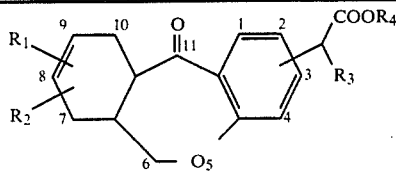

| Compound | (*) | $R_1$ | $R_2$ | $R_3$ | $R_4$ | M.p. (°C.) |
|---|---|---|---|---|---|---|
| 1 (Ex. 1h) | 2 | H | H | H | H | 112–113 |
| 2 (Ex. 1g) | 2 | H | H | H | $CH_3$ | B.p. 200° C. at 0.15 mbar |
| 3 (**) | 2 | 8-$CH_3$ | H | H | H | 133–134 |
| 4 | 2 | 8-$CH_3$ | 9-$CH_3$ | H | H | 166–167 |
| 6 | 2 | 10-$CH_3$ | H | H | H | 124–125 |
| 7 | 2 | 8-$nC_4H_9$ | 9-$nC_4H_9$ | H | H | oil |
| 8 | 2 | 8-$nC_2H_5$ | 9-$nC_2H_5$ | H | H | oil |
| 9 | 3 | H | H | H | H | 112–113 |
| 10 | 3 | H | H | H | $CH_3$ | B.p. 195–200 at 0.25 mbar |
| 11 (Ex. 3) | 3 | H | H | $CH_3$ | H | 158–160 |
| 12 | 2 | 8-$CH_3$ | H | H | H | 158–159 |
| 13 (Ex. 2b) | 3 | 8-$CH_3$ | 9-$CH_3$ | H | H | 168–170 |
| 14 (Ex. 2b) | 3 | 8-$CH_3$ | 9-$CH_3$ | H | $CH_3$ | 123–125 |
| 15 (Ex. 2c) | 3 | 8-$CH_3$ | 9-$CH_3$ | H | H | 167–169 [β] = +17,6° |
| 16 (Ex. 2c) | 3 | 8-$CH_3$ | 9-$CH_3$ | H | H | 167–169 [β] = +18,3° |
| 17 (**) | 3 | 8-$CH_3$ | H | $CH_3$ | H | 131–132 |
| 18 | 3 | 10-$CH_3$ | H | H | H | 95–100 |
| 19 | 3 | 8-$CH_3$ | 9-$CH_3$ | $CH_3$ | H | 139–142 |
| 20 | 3 | 8-$nC_4H_9$ | 9-$nC_4H_9$ | H | H | oil |
| 21 | 3 | 8-$iC_4H_9$ | 9-$iC_4H_9$ | H | H | oil |
| 22 | 3 | 7-$CH_3$ | 10-$CH_3$ | H | H | 164–166 |
| 23 | 3 | 9-$CH_3$ | H | H | H | 149–150 |
| 24 | 3 | 8-$C_2H_5$ | 9-$C_2H_5$ | H | H | oil |
| 25 | 3 | 8-$nC_3H_7$ | 9-$nC_3H_7$ | H | H | oil |
| 26 | 3 | 9-$CH_3$ | 8-$SC_6H_3$ | H | $CH_3$ | oil |
| 27 | 3 | 9-$CH_3$ | 8-$SO_2C_6H_5$ | H | $CH_3$ | 83–84 |
| 28 | 3 | 7-$CH_2$—$CH_2$—10 | | H | H | 131–133 |
| 29 | 3 | 8-CH=CH—CH=CH—9 | | H | H | 176–177 |

The compounds of the invention were subjected to pharmacological experiments which demonstrate their value as substances having therapeutic activity.

To study antiinflammatory activity, experiments were performed on the carrageenan-induced oedema test in rats according to the method of Winter et al. ("Carrageenan induced oedema in hind paw of the rat as an assay for antiinflammatory drugs". Proc. Soc. Exp. Biol. Med. 1962, 111, 544–547). The animals used are SPF Sprague Dawley male rats from Charles River (France), weighing 150 g on average, distributed randomly in batches using a distribution table.

The compounds are administered orally at doses of between 1 an 200 mg/kg, 1 hour before the injection of 0.1 ml of carrageenan, in a 1% strength suspension in sterile physiological saline, under the planar aponeurosis on one of the hind limbs. The control animals only receive placebo, a 1% strength solution of Tween 80. The increase in the volume of the limb is measured 3 hours after the injection of carrageenan by means of an Ugo Basile plethysmometer.

Results

Compared with the control animals, the animals treated with the compounds of the invention show a 40% decrease in the volume of the oedema at doses of 2 to 200 mg/kg. Furthermore, they have the unexpected property of not being ulcerogenic.

Other pharmacological experiments showed that the compounds of the invention are also active as analgesics and as inhibitors of platelet aggregation.

We claim:

1. A compound of formula (I)

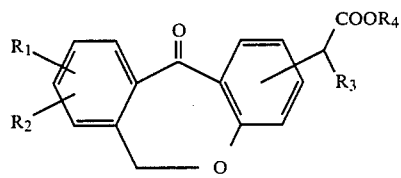

in which $R_1$ is hydrogen or $C_1$–$C_4$ alkyl and $R_2$ is hydrogen, $C_1$–$C_4$ alkyl, phenylthio or phenylsulfonyl or $R_1$ and $R_2$, together with the two carbon atoms 7 and 10, form an ethano bridge or, together with the two carbon atoms 8 and 9, form a fused benzene ring, $R_3$ is hydrogen or methyl and $R_4$ is hydrogen, $C_1$–$C_4$ alkyl or the cation of a base which is acceptable in pharmacology, the group $CH(R_3)COOR_4$ being at position 2 or 3.

2. A compound according to claim 1 wherein $R_3$ and $R_4$ are each hydrogen.

3. A compound according to claim 2 wherein $R_1$ and $R_2$ are each hydrogen.

4. A compound according to claim 2 wherein $R_1$ and $R_2$ are each methyl.

5. A compound according to claim 1 in the form of a racemate or an enantiomer substantially free from the corresponding enantiomer.

6. 8,9-Dimethyl-11-oxo-6,6a,7,10,10a,11-hexahydrodibenz[be]oxepin-3-acetic acid or a pharmacologically acceptable salt thereof which is in the form of a racemate or an enantiomer.

7. Dextrorotatory-8,9-dimethyl-11-oxo-6,6a,7,10,10a,11-hexahydrodibenz[be]oxepin-3-acetic acid or a pharmacologically acceptable salt thereof.

8. Pharmaceutical composition for treatment of inflammation, pain or undesirable platelet aggregation comprising an effective amount of a compound according to claim 1 in combination with a pharmaceutically acceptable excipient.

9. A composition according to claim 8 in unit dosage form.

10. A method for treating inflammation, pain or undesirable platelet aggregation in a human or non-human mammal body comprising administering an effective, non-toxic amount of a compound of formula (I) as defined in claim 1 to a human or non-human mammal in need thereof.

11. A method according to claim 10 comprising administering from 50 to 100 mg per day to the human or non-human mammal.

* * * * *

UNITED STATES PATENT AND TRADEMARK OFFICE
CERTIFICATE OF CORRECTION

PATENT NO. : 4,701,466

DATED : October 20, 1987

INVENTOR(S) : Thomas Purcell and Lydia Zard

It is certified that error appears in the above-identified patent and that said Letters Patent is hereby corrected as shown below:

In the Abstract correct the formula to read as follows:

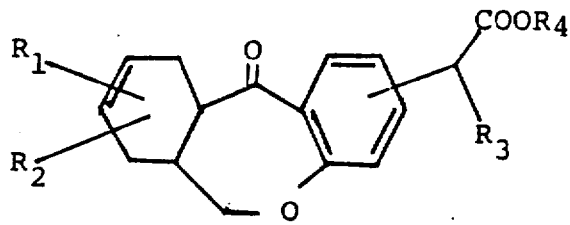

In Claim 1: correct the formula to read as follows:

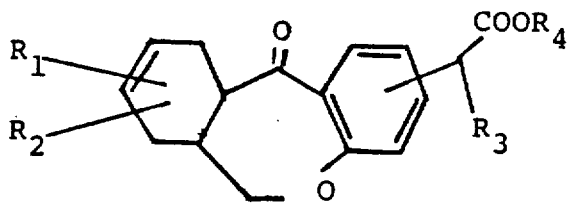

Signed and Sealed this

Eighteenth Day of October, 1988

Attest:

DONALD J. QUIGG

Attesting Officer

Commissioner of Patents and Trademarks